United States Patent [19]
Kaji

[11] Patent Number: 5,852,231
[45] Date of Patent: *Dec. 22, 1998

[54] ELUTION LIQUID CONTROL FOR A LIQUID CHROMATOGRAPH

[75] Inventor: Hironori Kaji, Hitachinaka, Japan

[73] Assignee: Hitachi, Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 814,845

[22] Filed: Mar. 11, 1997

[30] Foreign Application Priority Data

Mar. 29, 1996 [JP] Japan .................................. 8-075679

[51] Int. Cl.$^6$ .................................................. G01N 30/34
[52] U.S. Cl. .................... 73/61.56; 210/101; 210/198.2; 137/7
[58] Field of Search ................................ 73/61.52, 61.55, 73/61.56; 210/101, 198.2, 656, 741; 137/7, 8, 12, 88; 222/71

[56] References Cited

U.S. PATENT DOCUMENTS

| 4,032,445 | 6/1977 | Munk | 210/198.2 X |
|---|---|---|---|
| 4,128,476 | 12/1978 | Rock | 210/101 X |
| 4,233,156 | 11/1980 | Tsukuda et al. | 73/61.56 X |
| 4,595,495 | 6/1986 | Yotam et al. | 210/101 |
| 4,767,279 | 8/1988 | Dourdeville et al. | 210/198.2 X |

FOREIGN PATENT DOCUMENTS 63-3154 B2  1/1988  Japan .

*Primary Examiner*—Michael Brock
*Attorney, Agent, or Firm*—Kenyon & Kenyon

[57] ABSTRACT

In a low pressure gradient liquid chromatograph, two eluting liquids are transferred while they are being mixed with each other, whereby the mixing ratio thereof is changed with time. The mixing is performed by alternately opening and closing check valves provided in the liquid passages of the eluting liquids during a time period corresponding to the actual suction stroke of a plunger pump. The mixing ratio is determined by the time periods during which the check valves are opened, respectively. A detector is provided for detecting the pressure of the mixed liquid and the timing for opening and closing the check valves is changed in accordance with the detected pressure.

5 Claims, 6 Drawing Sheets

"PRIOR ART"

5,852,231

ELUTION LIQUID CONTROL FOR A LIQUID CHROMATOGRAPH

BACKGROUND OF THE INVENTION

The present invention relates to a liquid chromatograph, and more particularly relates to a liquid chromatograph suitable for performing liquid chromatographic analysis by varying the composition of an eluting liquid under a low pressure environment.

In a liquid chromatograph, it is one of the most important functions to supply to a column an eluting liquid which is called a mobile phase liquid by varying the mixing ratio of eluting liquids and thus the composition of the mixed eluting liquid. A liquid chromatograph which performs liquid chromatogaphic analysis by mixing a plurality of eluting liquids under a low pressure condition to vary the composition of the mixed eluting liquid is called a low pressure gradient liquid chromatograph. In that case, a pump disclosed, for example, in Japanese Patent Application Laid-Open No.63-3154 may be used as the liquid transferring pump for mixing eluting liquids and pumping the mixed eluting liquid.

FIG. 1 shows a system configuration of a conventional low pressure gradient liquid chromatograph. Two cams 5 and 6 are rotated by a motor 1 through pulleys 2 and 3 and a belt 4 mounted thereon. When the cams are rotated, a first plunger 7 and a second plunger 8 in pump cylinders are reciprocated. The plungers are inserted through plunger seals 20 and 21 into the cylinder the interior of which is filled with liquid. In the top portion and the bottom portion of the first pump cylinder 9, there are provided check valves 10 and 11 which respectively stop discharging in a suction stroke and sucking in a discharge stroke so that sucking and discharging of liquid are alternatively repeated by reciprocation of the plunger.

The second plunger 8 serves to make the flow on the delivery side continuous. Further, in some cases, a pressure detector, not shown, is provided in a flow passage on the delivery side and the flow is controlled based on the output signal using a control unit 12.

In the low pressure gradient liquid chromatograph, a plurality of eluting liquids are pumped while they are mixed, and the mixing ratio is changed with time. In this example, two eluting liquids 17 and 18 are mixed. The mixing of the eluting liquids in performed by alternatively opening opening-and-closing valves 15 and 16 comprising electromagnetic valves provided in the flow passages for the respective eluting liquids during a time period corresponding to an actual sucking stroke of the plunger pump under control of a control unit 12. The mixing ratio is determined by the time periods during which the opening-and-closing valves are opened. In the flow passage on the delivery side, there is a mixer 22 which mixes the mixed solution uniformly.

The control unit 12 recognizes operating positions of the plunger by detecting the rotating angle of the cams 5 and 6 for reciprocally moving the plungers, and the rotating angle of the cams 5 and 6 is detected by detecting the cut-off portion of a cut-off disk 13 secured to a cam shaft using a photo-interrupter 14.

The uniformly mixed eluting liquid is supplied to a column 26 through a sample injecting port 25. A sample is injected through the sample injecting port 25 into the column 26 and is eluted while passing through the column 26 so that sample components are separated from each other. The components separated thus are detected by a detector 27.

In the system described above, when pressure on the delivery side of the plunger pump is low, an accurate mixing ratio can be obtained. However, as the pressure on the delivery side becomes higher, the mixing ratio is varied because of compression of the seal, compression of the liquid and operating delay of the opening-and-closing valves. The reason is that the actual sucking time is shortened at a returning point of piston movement. That is, at the point where the piston movement changes from the discharge stroke to the suction stroke due to compression of the liquid, deformation of the seal and operating delay of the opening-and-closing valve, acting through the plunger. The point where suction begins is moved. The degree of the shortening of actual sucking time becomes larger as the pressure on the delivery side becomes higher. When the mixing ratio is changed depending on the pressure on the delivery side, it becomes difficult to identify the components since the retention time is varied.

SUMMARY OF THE INVENTION

An object of the present invention is to provide a liquid chromatograph which can correct the change in the mixing ratio of eluting liquids due to the pressure on the delivery side of a liquid transferring pump.

A liquid chromatograph according to the present invention comprises a column, a liquid transferring pump for mixing and supplying a plurality of eluting liquids through respective opening-and-closing valves to the column so as to elute a sample to separate components thereof from each other when the sample is injected into the column, a sample detector for detecting the separated components, a pressure detector for detecting discharge pressure of the liquid transferring pump, and a controller for controlling a mixing ratio of the eluting liquids by varying opening-and-closing timings of the opening-and-closing valves according to a detected output of the pressure detector.

Thorough use of the liquid chromatograph of the present invention, the change in the mixing ratio due to the pressure on the delivery side of the liquid transferring pump can be corrected.

DETAILED DESCRIPTION

Figure 1:
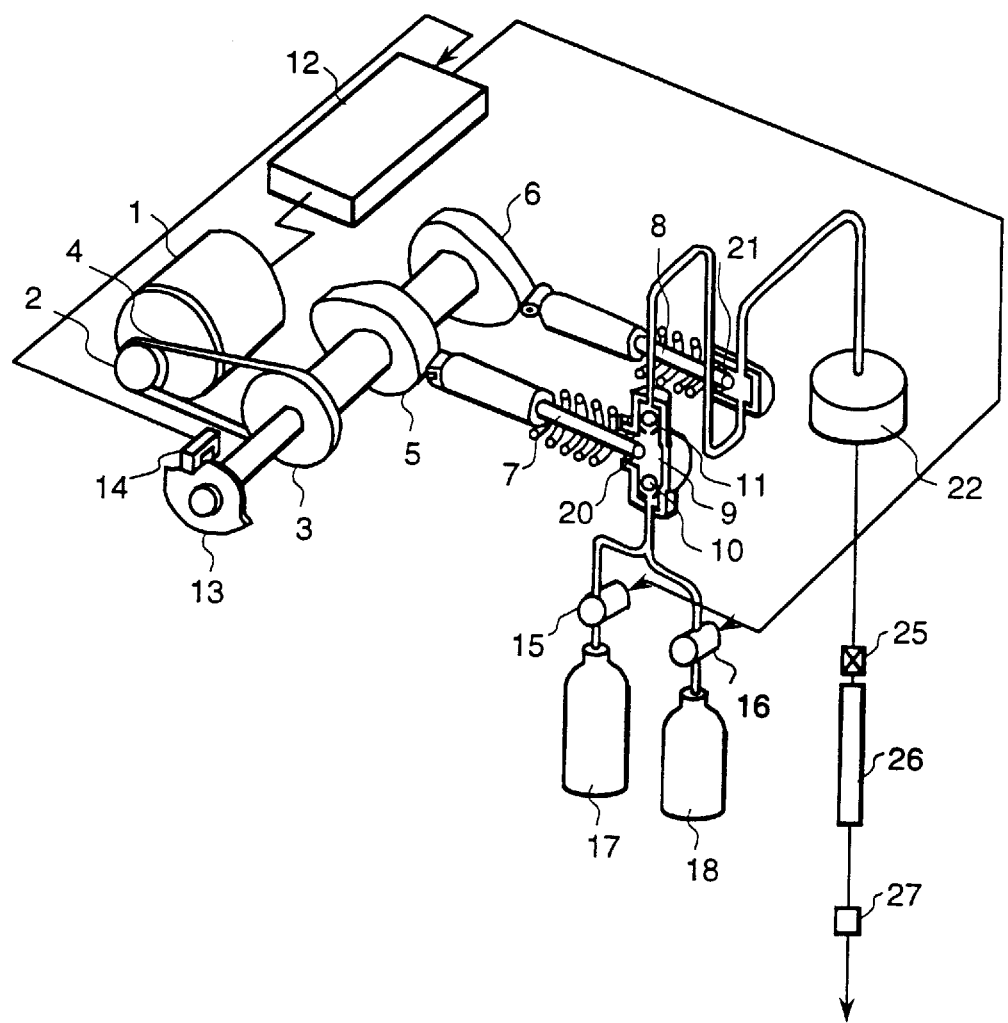
FIG. 1 is a schematic view of a conventional liquid chromatograph.
Figure 2:
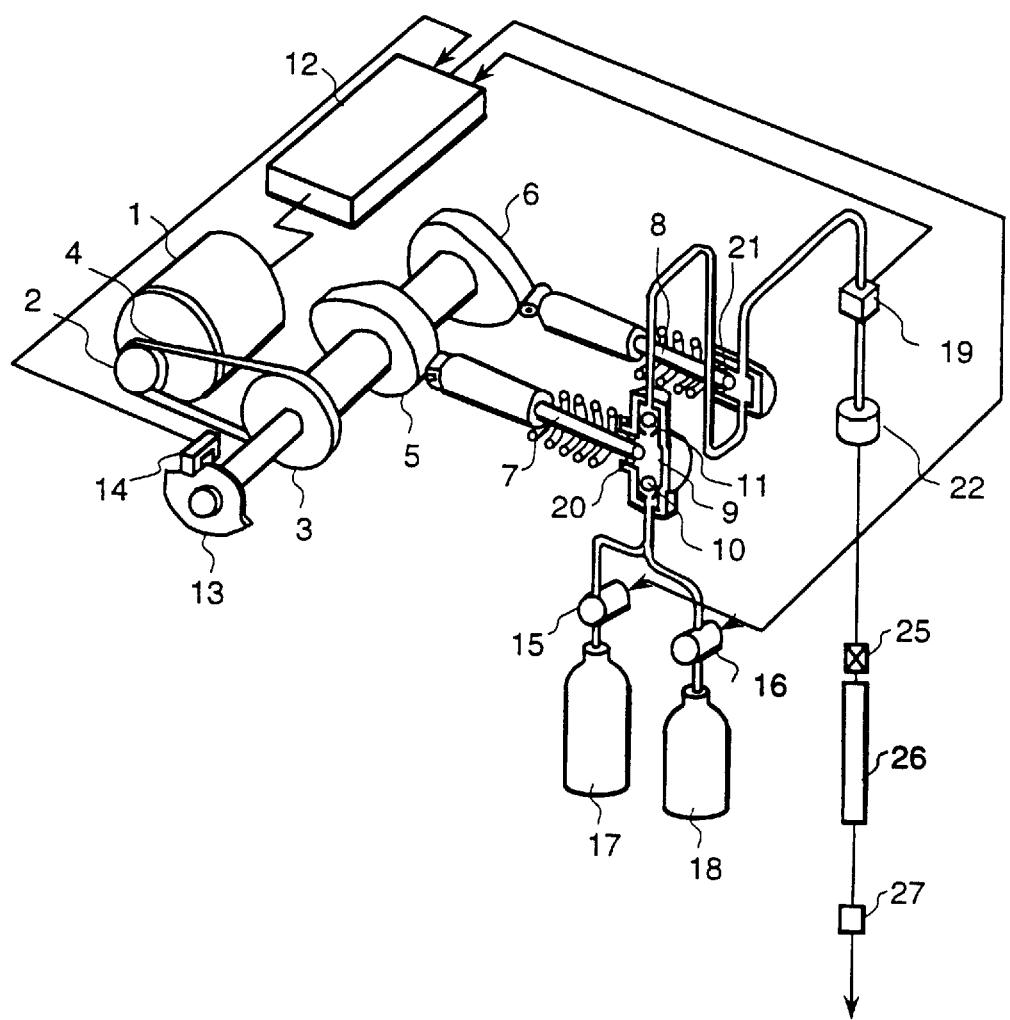
FIG. 2 is a schematic view showing an embodiment of a liquid chromatograph in accordance with the present invention.

An embodiment of the present invention will be described in detail below, referring to FIG. 2 to FIG. 6. In FIG. 2, the same elements as those shown in FIG. 1 are designated by the same reference numbers. A different point of the embodiment of FIG. 2 from FIG. 1 is that a pressure detector 19 is provided on the delivery side of the liquid transferring pump and outputs a signal which is input to the control unit 12 to control timings to open the opening-and-closing valves 15 and 16 based on the signal.

Figure 3:
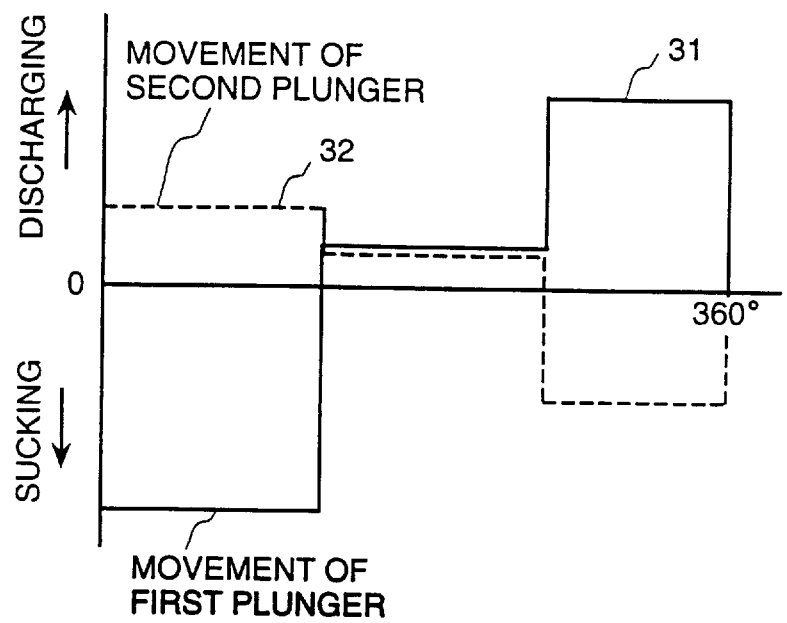
FIG. 3 is a graph explaining the operation of plungers of FIG. 2.

FIG. 3 shows operations of the first plunger 7 and the second plunger 8. In FIG. 3, the solid line 31 corresponds to sucking and discharging operations of the first plunger 7 and the broken line 32 corresponds to sucking and discharging operations of the second plunger 8. FIG. 3 shows one cycle of liquid-transferring of the pump which is shown in relation to the rotating angle of the cams 5 and 6. When the first plunger 7 is in a sucking operation, the second plunger 8 is in a discharging operation. When the second plunger 8 is in a sucking operation, the first plunger 7 is in a discharging operation. This example includes processes in which the both plungers perform discharging operation. As having been described in connection to FIG. 1, the control unit 12 recognizes operating positions of the plungers by detecting the rotating angle of the cams 5 and 6 for reciprocating the plungers, and the rotating angle of the cams 5 and 6 is detected by detecting the cut-off portion of a cut-off disk 13 secured to a cam shaft using a photo-interrupter 14.

As shown in FIG. 3, the eluting liquid is intermittently sucked. However, a desired mixing ratio of the eluting liquid and thus the composition of the mixed eluting liquid can be obtained by controlling the opening-and-closing values 15 and 16 so as to alternatively switch time periods for which the opening-and-closing valves 15 and 16 are opened during an actually sucking time interval corresponding to the desired mixing ratio.

Figure 4:
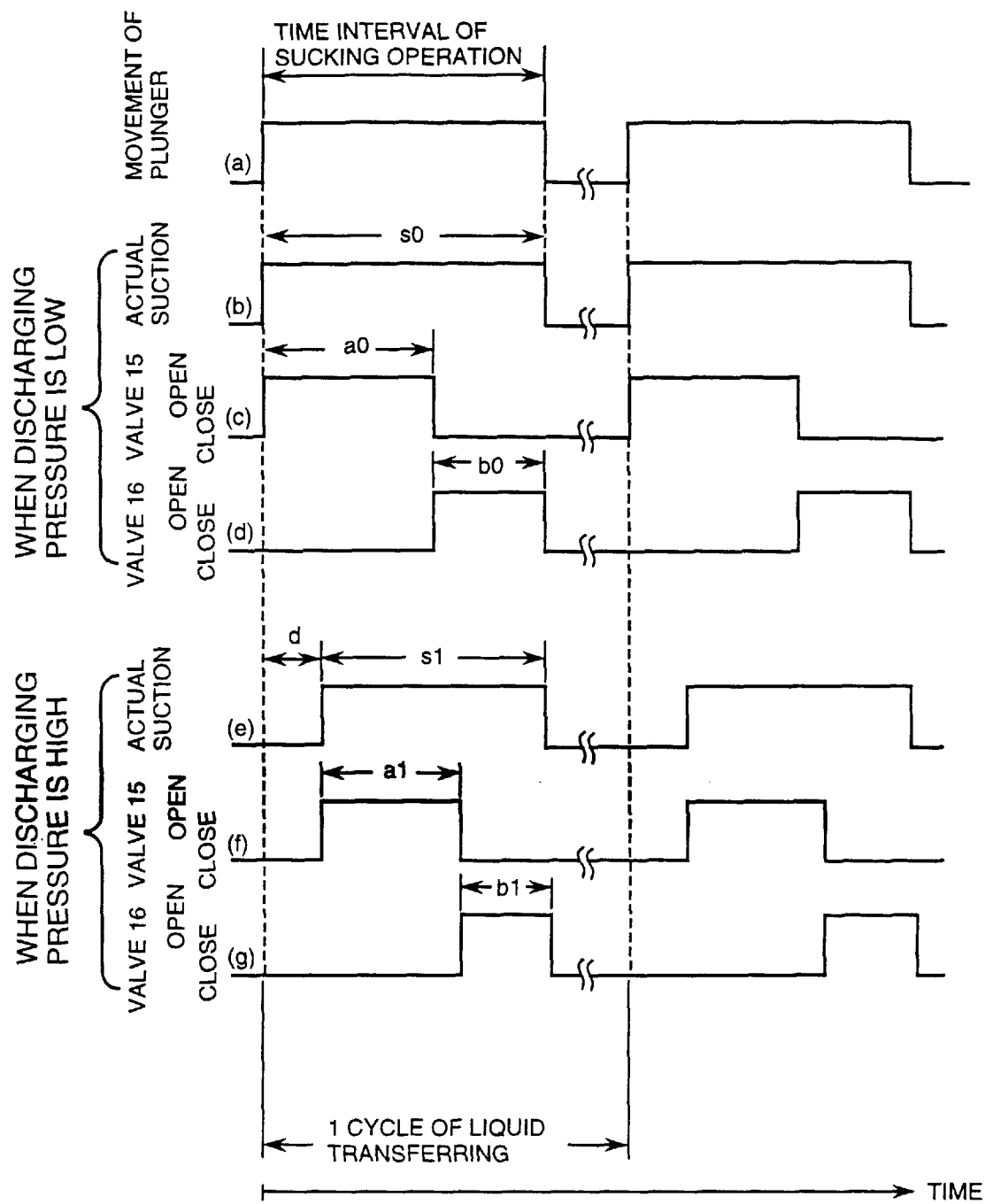
FIG. 4 is a chart showing a relationship between movement of plungers, movement of opening-and-closing valves and timings of sucking liquids in the embodiment of FIG. 2.

FIG. 4 shows operation of the opening-and-closing valves 15 and 16 during the suction stroke. Movement of the first plunger 7 is shown in the top of FIG. 4. The plunger 7 performs sucking operation in the time interval P. Where the discharging pressure is low, the actual sucking agrees with the movement of the plunger 7, that is, the actual sucking time interval so becomes equal to P. Therein, a ratio of the time $a_0$ for which the opening-and-closing valve 15 is opened and the time $b_0$ for which the opening-and-closing valve 16 is opened becomes a mixing ratio. However, as the discharging pressure is increased, the actual liquid sucking time interval does not agree with movement of the plunger due to deformation of the seal, compression of the liquid and operating delay of the opening-and-closing valve, and starting time of suction is delayed. Letting the delayed time be d, the actual suction time interval is expressed by $s_1$. As the discharging pressure is increased, the delay becomes larger.

In the embodiment in accordance with the present invention, switching timings of the opening-and-closing valves 15 and 16 are varied as shown in the lower portion of FIG. 4. That is, when a mixing ratio is expressed by R, the opening-and-closing valves 15 and 16 are opened for the time expressed by the following equations.

The time interval for which the electromagnetic valve 15 is opened is:

$$a_1 = R \times S_1$$

The time interval for which the electromagnetic valve 16 opened is:

$$b_1 = (1-R) \times S_1$$

Therein, the value $S_1$ is an actual sucking time interval which is expressed by $S_1 = P - d$. The value d expresses a time interval from the time when the plunger starts sucking operation to the time when sucking actually starts. The value d is a function of the discharging pressure. In this embodiment of the present invention, the value d is assumed to be a value proportional to the discharging pressure.

It would be understood from the above description that the time of a turning point at which movement of the plunger changes from suction to discharge is detected by a timing detecting system composed of the cut-off disk 13, the photo-interrupter 14 and the control unit 12, and a time interval from receiving the time of the turning point to opening the opening-and-closing valves 15 and 16 is controlled based on the signal detected by the pressure detector 19.

Figure 5:
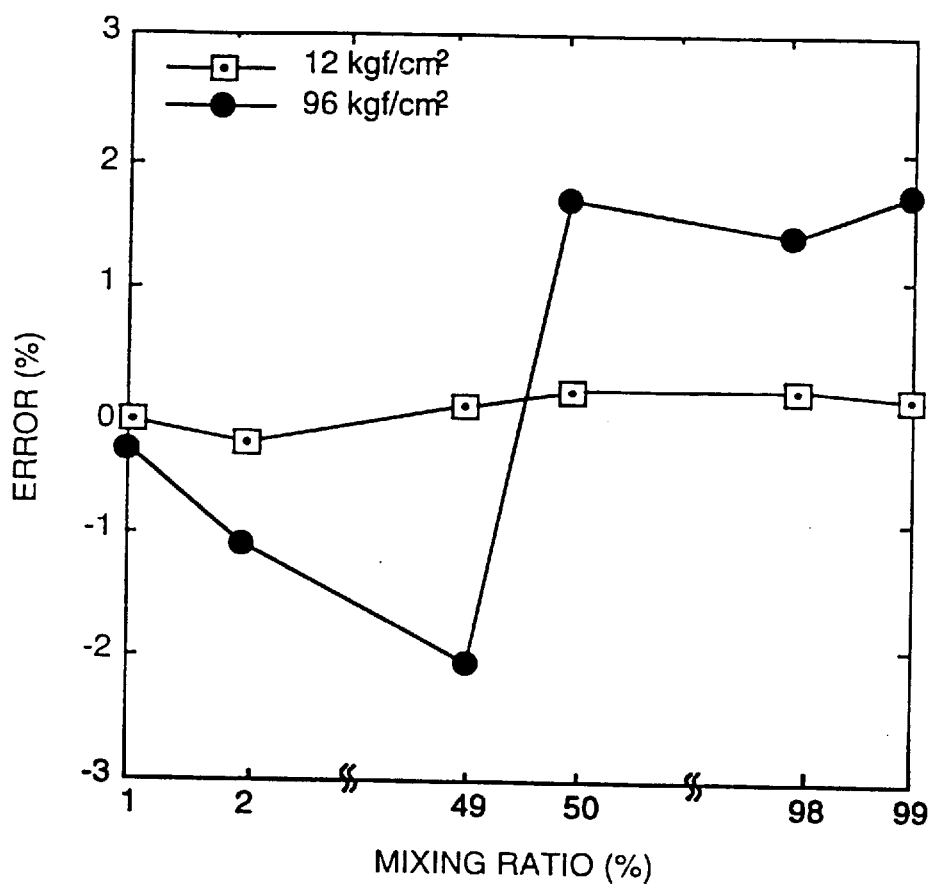
FIG. 5 is a graph showing measured results on accuracy of the mixing ratio in the conventional technology.
Figure 6:
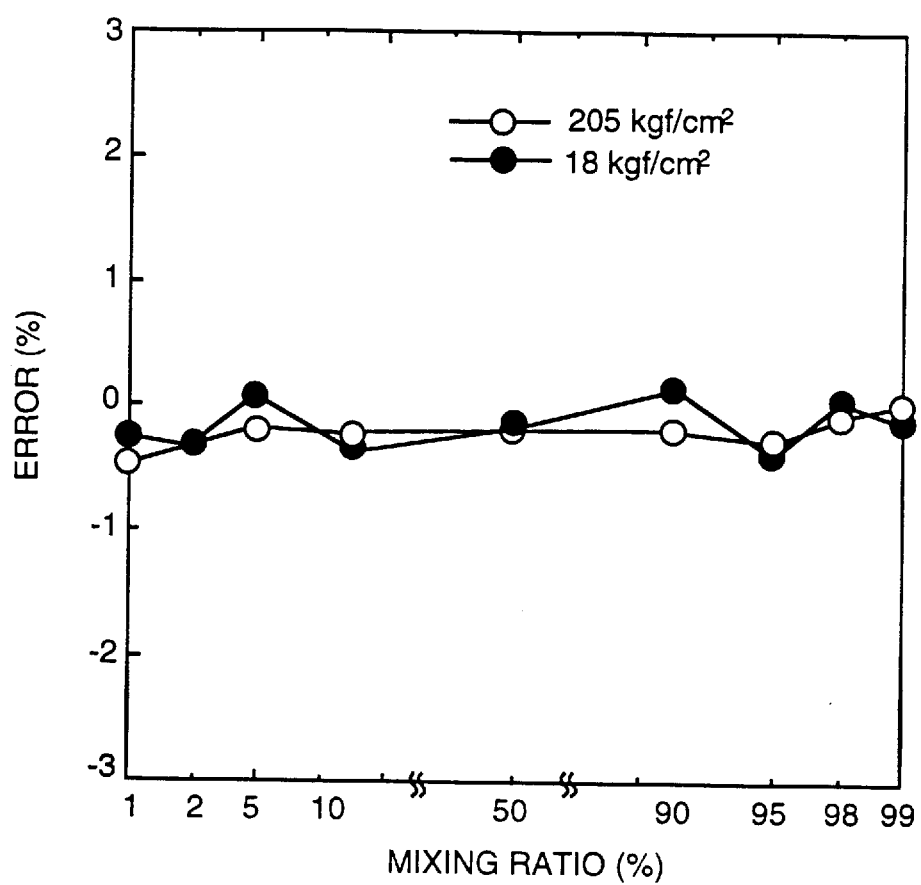
FIG. 6 is a graph showing measured results on accuracy of the mixing ratio in an embodiment in accordance with the present invention.

FIG. 5 and FIG. 6 show examples of measured results on accuracy of the mixing ratio of the mixed eluting liquid. FIG. 5 shows measured results in the conventional technology. When the discharging pressure is high, the error is large. On the other hand, FIG. 6 shows measured results obtained in the embodiment in accordance with the present invention. It would be understood that accurate mixing ratios can be obtained even when the discharging pressure is high.

The following are embodiments in accordance with the present invention other than the above embodiment.

Although in the above embodiment the opening-and-closing valve is kept closed during the time period when suction is not actually performed, the opening-and-closing valve may be opened.

Although two eluting liquids are mixed in the above embodiment, the same operation may be performed in a case where three or more kinds of eluting liquids are mixed. In that case, the time interval opening each of the opening-and-closing valves is determined corresponding to the time interval $s_1$ of actual sucking operation.

Further, although the value d is assumed to be a value proportional to the discharging pressure in the above embodiment, a function having an arbitrary form obtained from an experiment may be employed as the value d.

The aforementioned embodiment corrects a time difference between the starting time of movement of the plunger suction stroke and the actual starting time of sucking the liquid. However, there is a time difference between the ending time of movement of the plunger suction stroke and the actual ending time of sucking the liquid. This time difference can be also corrected in the same manner.

According to the embodiment of the present invention, it is possible to provide a liquid chromatograph which can correct the change in a mixing ratio of eluting liquids due to the pressure on the discharging side of a liquid transferring pump.

Since it is obvious that many changes and modifications can be made in the above described details without departing from the nature and spirit of the present invention, it is to be understood that the present invention is not to be limited to the details described herein.

What is claimed is:

1. A liquid chromatograph, comprising a column, a liquid transferring pump for mixing and supplying a plurality of eluting liquids through respective opening-and-closing valves to said column so as to elute a sample to separate components thereof from each other when said sample is injected into said column, a sample detector for detecting said separated components, a pressure detector for detecting discharge pressure of said liquid transferring pump, and a controller for controlling a mixing ratio of said eluting liquids by varying opening-and-closing timings of said opening-and-closing valves according to a value of the discharge pressure detected by said pressure detector such as to shorten the period of time during which each opening-and-closing valve is opened as the value to the detected discharge pressure becomes larger.

2. A liquid chromatograph according to claim 1, wherein said liquid transferring pump comprises a plunger pump, and said controller alternatively opens and closes said opening-and-closing valves during a time period corresponding to a suction stroke of said plunger pump to mix said plurality of eluting liquids.

3. A liquid chromatograph according to claim 2, wherein said plunger pump comprises a cylinder, a plunger which is so reciprocated as to suck said plurality of eluting liquids in said cylinder through said respective opening-and-closing valves and to discharge said sucked eluting liquids, and check valves for stopping discharging said eluting liquids during said suction stroke and stopping sucking the eluting liquids during a discharge stroke of said plunger pump.

4. A liquid chromatograph according to claim 2, wherein said plunger pump comprises a cam for reciprocating said plunger and said controller comprises a timing detector for detecting a timing when movement of said plunger is at a returning point on the basis of a rotating angle of said cam and controls a time interval from the time of receiving a detected output signal of said timing detector to the time of opening said opening-and-closing valve corresponding to the discharge pressure detected by said pressure detector.

5. A liquid chromatograph according to claim 3, wherein said plunger pump comprises a cam for reciprocating said plunger and said controller comprises a timing detector for detecting a timing when movement of said plunger is at a returning point on the basis of a rotating angle of said cam and controls a time interval from the time of receiving a detected output signal of said timing detector to the time of opening said opening-and-closing valve corresponding to the discharge pressure detected by said pressure detector.

\* \* \* \* \*

UNITED STATES PATENT AND TRADEMARK OFFICE
CERTIFICATE OF CORRECTION

PATENT NO.   : 5,852,231
DATED        : 22 December 1998
INVENTOR(S)  : Hironori KAJI et al.

It is certified that error appears in the above-indentified patent and that said Letters Patent is hereby corrected as shown below:

| Column | Line | |
|--------|------|--|
| 1 | 45 | Change "in" to --is--. |
| 2 | 8  | Change "at a returning" to --at the returning--. |
| 3 | 38 | Change "time ao" to --time $a_o$--. |

Signed and Sealed this

Second Day of November, 1999

Attest:

Q. TODD DICKINSON

*Attesting Officer*   *Acting Commissioner of Patents and Trademarks*